(12) United States Patent
Prichep

(10) Patent No.: US 6,556,861 B1
(45) Date of Patent: Apr. 29, 2003

(54) FETAL BRAIN MONITOR

(75) Inventor: Leslie S Prichep, Mamaroneck, NY (US)

(73) Assignee: New York University, New York, NY (US)

(*) Notice: Subject to any disclaimer, the term of this patent is extended or adjusted under 35 U.S.C. 154(b) by 117 days.

(21) Appl. No.: 09/716,517

(22) Filed: Nov. 20, 2000

(51) Int. Cl.[7] .............................. A61B 5/04; A61B 5/00; A61N 1/08
(52) U.S. Cl. ......................... 600/544; 600/559; 607/45
(58) Field of Search ............................ 600/544–545, 600/300, 559; 607/45, 48, 62; 128/510

(56) References Cited

U.S. PATENT DOCUMENTS

| | | | | |
|---|---|---|---|---|
| 4,705,049 A | * | 11/1987 | John | 600/544 |
| 4,913,160 A | * | 4/1990 | John | 600/544 |
| 5,491,756 A | * | 2/1996 | Francais | 381/332 |
| 6,016,444 A | * | 1/2000 | John | 128/910 |
| 6,066,163 A | * | 5/2000 | John | 607/45 |
| 6,067,467 A | * | 5/2000 | John | 600/544 |
| 6,196,977 B1 | * | 3/2001 | Sininger et al. | 600/545 |

* cited by examiner

Primary Examiner—William C. Doerrler
(74) Attorney, Agent, or Firm—Pay Kaplun & Marcin LLP

(57) ABSTRACT

A Fetal Brain Monitor (FBM) utilizes a transducer which is placed on the abdomen of a mother and which is pulsed to generate auditory sounds, i.e., clicks, to provide auditory brainstem evoked responses (BAER) of a fetus within the mother's uterus. The fetus' brain waves are detected by a biosensor, amplified, converted to digital data, and analyzed, in one embodiment, using a digital comb filter to improve the signal/noise ratio. The computer system uses QEEG (Quantitative EEG) to compare the data from the fetus to normative data or to prior states of the fetus' own data (self-norm)

20 Claims, 3 Drawing Sheets

FETAL BRAIN MONITOR

FIELD OF THE INVENTION

The present invention relates to medical obstetric procedures and devices and more particularly to the non-invasive monitoring of the human fetus while in the mother's uterus.

BACKGROUND OF THE INVENTION

At the present time it is conventional, in medical practice, to ascertain the status and health of a human fetus by ultrasound. Typically a pregnant female may undergo 1 to 4 ultrasound examinations during her pregnancy.

In addition, the heart of the fetus will be detected and monitored using a stethoscope. It is also conventional to monitor the heartbeat of a neonate (newly born infant) during and immediately after childbirth, using a stethoscope or a more sophisticated analysis instrument.

After childbirth, the status of pre-term neonates may be ascertained using EEG (electroencephalography).

An EEG (electroencephalograph) procedure measures neurophysiological activity by measuring the intensity and pattern of electrical signals generated by the brain. Undulations in the recorded electrical signals are called brain waves. The entire record of electrical rhythms and other electrical activity (ongoing background signals and event related transients) of the brain is an EEG. EEGs are widely used to assist in the diagnosis, in children and adults, of epilepsy, brain tumors, physiological disorders and other brain abnormalities. Because the electrical waves produced by an injured or abnormal brain will differ in predictable ways from waves produced by a normal brain, an EEG exam should disclose and help diagnose brain abnormalities and injuries.

Although EEG based brain monitoring of patients has been performed for over 70 years, it is only recently, with the advent of computers and new analysis techniques, that medical professionals have begun to recognize the benefits of EEGs as a broad based diagnostic tool. This should be contrasted with the field of cardiac monitoring in which medical professionals have long been aware of the benefits of monitoring, and have integrated electrocardiogram ("ECG") procedures into both preventive and diagnostic health care. As a result, medical device and instrument companies have concentrated on, and provided improved technology for, the fetal cardiac monitoring market. However, EEG technology has not been applied, in general medical usage, to determine the health or status of a fetus.

It has been generally considered that meaningful data could not be gathered non-invasively from the brain of a fetus.

The fetus lies within the uterus surrounded by amniotic fluid. The uterus is within the abdominal cavity of the mother and it is surrounded by layers of skin, muscle and blood. The thickness of the uterine wall and the amount of amniotic fluid vary greatly among different mothers. Consequently, it is difficult to believe that meaningful brain wave signals could be obtained from the fetal brain through all those layers of material. The adult brain produces brain waves in the microvolt range and the fetal brain's brain waves are weaker than those of a child or adult.

A series of scientific articles have been written about the EEG of neonates. Specifically, tests have been conducted on pre-term at risk neonates (newly born babies) using auditory brain stem auditory evoked response (BAERs). In this BAER procedure a sound (auditory) is transmitted to the neonate. One, or preferably 3 or more, electrodes are placed on the baby's scalp and the baby's brain waves are detected as the neuronal responses propagate along the auditory pathways from the auditory nerve to the thalamus. By averaging a series of such responses to the sound, it is possible to identify components of the response which are reproducible, the "evoked responses" of the neonate's brain are synchronous with the sounds. The "evoked response" is in a time-locked relationship to the auditory stimuli (Taylor 1996; Pasman 1997; Singh 1998; Mercuri 1994; Yasuhara 1986; Cycowisz 1988; Murray 1988; Majnemer 1988; Cox 1992 and Hayakawa). The articles are cited by lead author and date and the patents by patent numbers. They are listed below and are incorporated by reference herein.

Several articles have reported selective vulnerability of auditory nuclei in the pre-term period, especially between 28 and 40 weeks gestational age (GA) (Griffiths, Leech). There have been several reports on the clinical utility of BAERs in newborn infants, particularly with full term infants having asphyxia or hyperbilirubemia or at risk for hearing loss. Neonatal BAER abnormalities have been found in infants with perinatal (at the time of birth) complications (Yashuhara, Cycowisz, Murray). Prognostic value of term BAER assessments has been suggested in studies of later language skills or neurodevelopmental outcome in high risk neonates (Karmel, Majnemer) with low birth weight (Cox) or with neurological signs and demonstrable brain anomalies (Salamy). While all of these reports related to full-term infants, it seems reasonable to propose that the BAER abnormalities existed before delivery and that intrauterine measurements might have provided an early warning of such abnormalities.

In Maynard U.S. Pat. No. 4,308,873 it is suggested that the ongoing EEG of a fetus may be detected by separating the EEG signals from electrocardiograph (ECG) signals. Electrodes are placed directly on the scalp of the fetus during labor (after separation from the uterus).

SUMMARY OF THE INVENTION

In accordance with the present invention, the brain waves of the fetus are non-invasively detected and analyzed in a "Fetal Brainstem Monitor" (FBM). This is a very difficult procedure and requires highly sophisticated techniques and sensitive equipment. However, the evaluation of fetal brain waves may permit the assessment of conditions which may lead to abnormal or delayed intrauterine development and provide a standard for normal fetal development.

It is important, in order to detect such faint fetal brain waves, that they be timed in response to a stimuli. The preferred stimuli are auditory. Preferably a sound generator, for example of click sounds, is placed on the belly of a pregnant woman. The click sounds are transmitted through her skin, muscles, womb and amniotic fluid, to the ears of the fetus. Such transmission of sound is possible because sound travels well through fluids.

One, or more, detecting biosensor electrodes are removably placed on the skin of the mother, proximate her womb. Preferably the electrode is a disposable biosensor which uses an adhesive hydrogel material. It does not require skin preparation or collodion and should provide a low electrical impedance (under 5000 ohms).

The biosensor electrode detects the faint micro-volt level brain waves of the fetus. Because of the faintness of the signals, the amplification which is required is much greater than with conventional EEG amplifiers. In addition, the amplifier should be low in internal noise. Preferably the amplifier connected to the biosensor electrode should have a gain of 200,000 and a noise level of less than 1 microvolt.

The analysis of the EEG is performed using advanced filtering techniques and algorithms relating to Quantitative EEG ("QEEG"). These techniques are critical to obtaining meaningful data from the faint electrical brain waves of the fetus. For example, the fetus in the embryonic sac is in almost constant movement, which is considered a muscle artifact and generates noise which may drown out the brain wave signals.

In addition to noise generated by movement of the fetus, the maternal environment produces other noises. These include the heartbeats of the fetus and the mother, movements of the mother (muscle artifacts) such as breathing and eye blinking and the mother's brain waves, including the mother's brain wave response to the auditory stimuli.

The following are some of the quantitative approaches to improve the signal-to-noise ratio in this difficult EEG environment.

1. The BAER (Brainstem Auditory Evoked Potentials) are time-locked to the auditory stimuli. The responses are in the interval 1–10 milliseconds (MS) after the stimulus. This time window permits the Fetal Brainstem Monitor (FBM) to receive data only during that period (1–10 MS) following an auditory stimulus. In addition, the elapsed time after each stimulus (latency) of the peak responses of each portion of the brain stem are known, so that data which falls outside of the expected range is discarded. Specifically, the sequence of peaks in the waveshapes of such evoked responses, and the peak amplitudes, reflect activation of the acoustic nerve, cochlear nucleus, superior olivary complex, lateral lemniscus, inferior colliculus, medial geniculate, and auditory cortex.

2. Preferably the fetal brain wave signals, after analog-to-digital conversion, will be subjected to "optimal digital filtering." Such filtering removes contaminating noise, in almost real-time (2–5 seconds). This is an adaptation of an optional digital filtering.

3. A procedure involving FFT (Fast Fourier Transform) and IFFT (Inverse Fast Fourier Transform) is used to extract the faint fetal brain waves from the background noise. In a preferred embodiment the procedure uses the following steps:

(a) A "light average" (about 50–500 samples) of data are collected, for example, the BAERs, to 200 auditory stimuli. This is the signal "S".

(b) The same size light averages of data, in the absence of stimuli, is collected for the noise "N".

(c) A number of sets of data representing the signal "S" and noise "N" are collected, for example, 10 sets of each. In this example, 2000 stimuli would be generated to produce 10 sets of "S" data.

(d) A FFT is made of each data set, e.g., 10 of N and 10 of S.

(e) For each resulting pair of FFT (each "bin" of FFT is one data set of N and one of S), the F-ratio is computed. The F-ratio, in this case, is the Phase Variance S/Phase Variance N.

(f) A threshold has been set, based on prior experience, for an acceptable F-ratio, i.e., a significant value of F-ratio.

(g) The phase variance F-ratios are scanned for all frequencies of FFT from 0 to 5 KHz.

(h) For those frequencies where the F-ratio is not significant, set the coefficients to zero.

(i) perform an IFFT on the remaining terms (the non-zero terms.

(j) average the IFFT, which provides relatively noise-free signals.

Preferably the entire procedure (a)–(j) is repeated (iteration), for example, three times, to provide the final result. In terms of time, the 2000 stimuli and equal non-stimuli time, may take less than 3 minutes and the entire test (3 iterations) would take less than 9 minutes.

4. "Neurometric" analysis is applied to determine if data is within the bounds of expected signals defined by normative data and the statistical significance of each peak in the fetal brain wave data. Neurometric analysis is a statistically based set of techniques and algorithms which collects data from normal groups of developing fetuses. The fetus being monitored at each state of fetal development is compared to the "normal" group to ascertain if the BAERs are normal or abnormal and, if abnormal, the locus, extent and nature of the abnormality. In another embodiment, the state of the fetal brain is assessed relative to an initial state in the fetus and the fetus serves as its own "norm." Such self-norming allows comparison of successive measurement relative to some prior state.

BRIEF DESCRIPTION OF THE DRAWINGS

The following detailed description is of the inventor's presently known best mode of practicing the invention and should be taken in conjunction with the accompanying drawings.

In the drawings.

The details of the preferred embodiments of such neurometric analysis are set forth in the following detailed description of the invention, which also describes the details of the digital comb filter and preferred methods of artifact rejection.

DETAILED DESCRIPTION OF THE INVENTION

Figure 1:
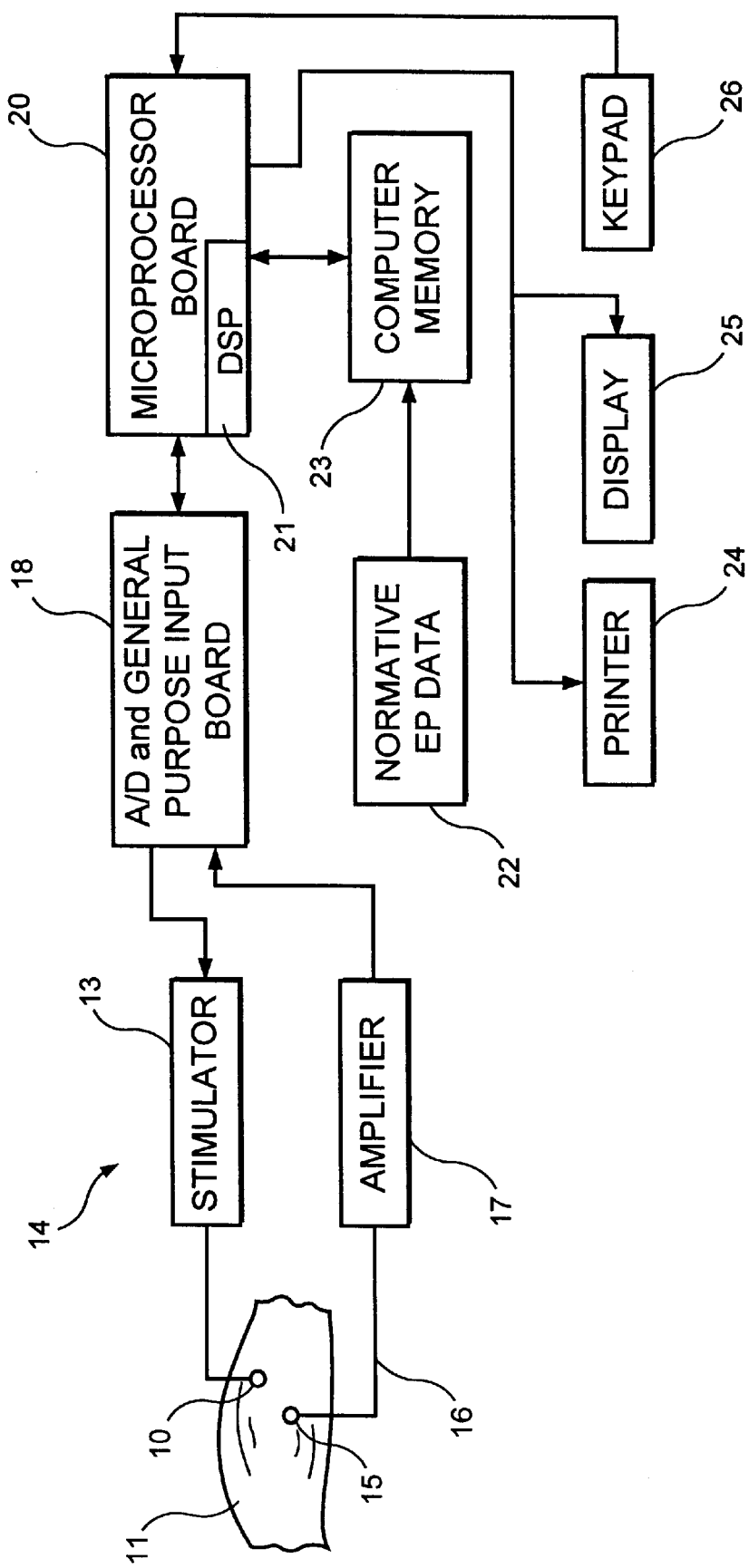
FIG. 1 is a block circuit diagram of the Fetal Brain Monitor (FBM) of the present invention.

As shown in FIG. 1, an auditory stimulus transducer 10 is removably positioned on the skin of the abdomen 11 of a pregnant human female. The transducer may be similar to those used to generate ultrasonic sounds in an ultrasonic fetal examination, except that it operates in the auditory range (below 15,000 Hz). In a preferred embodiment a small audio loudspeaker is physically coupled, at one end, to a cylinder filled with a saline solution with the other end covered by a thin rubber membrane. The loudspeaker is driven by the stimulator 13 (stimulus generator) of the FBM (Fetal Brain Monitor) 14.

The rate, amplitude and duration of the sound pulses are preferably similar to those used for BAER monitoring of children and adults. Sound is transmitted well through fluid media. The transducer 10 will deliver the necessary energy to the skin, given the mechanical compliance of the transducer system (the speaker coupled to the fluid-filled cylinder). The maximum pulse repetition rate which is compatible with efficient transmission using this transducer system is not presently known. This maximum repetition rate is a limiting factor on the speed with which Brainstem Auditory Evoked Response (BAER) might be acquired from a fetus. The transducer may deliver rarifaction, condensation or filtered clicks; or in another embodiment, vibratory stimulation, delivered by mechanical tapping of the abdominal wall.

One or more biosensor electrodes are also removably placed on the mother's abdomen to detect fetal brain waves. As shown in FIG. 1, a single electrode 15 is positioned on the abdomen, preferably not close to the transducer 10. The electrode preferably is a pre-gelled self-adhesive disposable electrode (such as a "Hydrodot" ™, Physiometrix, Mass., or an EEG electrode). This pre-gelled disposable biosensor attaches to a reusable lead wire 16 and is an alternative to a conventional EEG cup electrode. Alternatively, the electrode 10 may have multiple small barbs, a needle electrode or a conductive disk, which is removably attached to and may penetrate the patient's skin; the electrode may also use conductive gel, providing rapid attachment and acceptably low noise, and may be sterile and disposable. In this, and in other embodiments, a self-adhering electrode may be used, for example, the "ZIP-PREP" ™ electrode having stainless micro-barbs in an adhesive gel patch, the patch being applied with finger pressure.

As shown in FIG. 1, the lead wire 16 is the input to a high-gain low-noise amplifier 17 of FBM 14. The amplifier 17 amplifies analog brain wave signals. Preferably the amplification gain is about 200,000. The amplifier has a high input impedance (1 Megohm), a bandwidth of 100 Hz to 500 K Hz, and a noise level of less than 1 microvolt. The analog output of amplifier 17 is converted to digital data by the analog/digital converter 18 which operates at a minimum rate of 20,000 samples per second and a resolution of 16 bits. The FBM 14 includes a software programmed microprocessor board 20 having a Central Processor Unit (CPU) and a Digital Signal Processor (DSP) 21. The microprocessor and DSP may be portions of a laptop computer or PC. The microprocessor and DSP perform the following functions: (i) they provide a timed sequence of audio stimulations to the patient, such as an audio tone or click at one repetition rate; and (ii) based on the responses to these stimulations, they test the functional state of the fetal brain stem (Brainstem Auditory Evoked Response—BAER). FBM 14 uses a computer system based on a conventional microprocessor, such as an Intel Pentium III ™ and has a limited internal memory, for example, 1 Gigabyte (hard disk)and 500 Meg of RAM. The amplifier 17 is connected to an analog-to-digital converter (A/D) and multiplexer within General Purpose Input Board 18 (GPIB). The computer memory 23 contains a normative or reference EP database 22.

A printer 24 may be used to print out a report on the patient. A series of such reports from the same fetus may be assembled to give a picture of brainstem development longitudinally during gestation or of momentary brainstates during stages of delivery. The results of the analysis are shown on display 25, which may be a monitor. The keyboard 26 is used to enter data into the FBM.

The analog-to-digital multiplexer (A/D multiplexer) 18 provides a digital output from the analog amplifier. The data from the multiplexer is transmitted to a microprocessor board 20. The microprocessor has been programmed by an external software program means, such as a floppy disk recorder, or other input system, such as read-only memory (ROM). The programmed microprocessor ("firmware") is programmed to perform the data acquisition and the data analysis described below.

The program and its controlled microprocessor condition the input signals and insure that they are valid biological signals, including automatic artifact rejection and periodic automatic calibration testing and impedance measurements.

The fetus is audio-stimulated by the stimulator 13 under control of the microprocessor board 20.

The FBM computer system 14 automatically provides a timed set of stimuli. The fetus' brain waves will respond to each stimulus with a component of frequency $F_1$ in the EEG power spectrum, providing an "Evoked Potential" (EP). Those brain waves may be averaged, time-locked to stimuli onsets to improve the signal/noise ratio, providing an "Average Evoked Response" (AER). However, preferably a digital comb filter is used to reduce the adverse effects of noise, see U.S. Pat. No. 4,705,049. Filtering and splitting algorithms may reduce low-frequency noise and remove artifact contaminated samples prior to averaging. Alternatively, other methods for enhancing signal-to-noise ratios may be used, such as very narrow band (VNB) FFT at the repetition rate of the stimulator. In this embodiment, VNB FFT would be performed in successive samples and the power at each frequency averaged across the set of samples. While this method would not provide wave shape details, it would provide an indication of responsivity on the fetal auditory system.

The AER is the sum of N samples time-locked to the onset of stimuli divided by the number of samples, to provide an updated average. N will vary depending upon the sensory modality. The AERs are held in computer memory 23.

The amplifier 17 has an input isolation circuit to protect against current leakage, such as a photo-diode light-emitting diode (LED) isolation coupler. The amplifier 17 is protected from electrical interference by a radio-frequency filter and a 60-cycle notch filter.

EEG recordings may be contaminated by voltages arising from body movements, eye motion or other causes. These artifacts, it is assumed, based on prior studies, generate voltages larger than the brain wave voltage. An updating voltage threshold is computed continuously for the EEG channel or, if more than one channel, separately for each channel by calculating the root mean squared (r m s) voltage, for example, for a sliding 20-second window, and multiplying it by an appropriate constant (r m s voltage is approximately 0.2 standard deviations of amplitude). Segments containing voltages at any time point which are larger than this updated threshold are rejected, unless this option is turned off by attending personnel. Sampling is suspended, for example, for one second, to avoid increasing the threshold by incorporating the artifact. It is then resumed. Preferably those intervals (recording periods on each EEG channel) are rejected in which the voltage (signal) exceeds a multiple of the r m s voltage equal to 6 times (6x) the standard deviation of amplitude. Alternatively, an absolute maximum voltage threshold may be installed. This voltage threshold method provides segments of relatively artifact-free EP data. The computer system, in effect, stitches these intervals together to form a continuous artifact-free EP sample, which is recorded in the computer memory.

Because critical decisions may depend upon the accuracy of the evaluation, ideally odd and even split halves may be constructed by assigning intervals alternately to two interlocked but independent samples, each containing 32 light averages which are derived from 64 stimuli. The standard deviation (6 ) within each such split-half sample can be computed at each sample point of the light averages;

$$\sigma^2 = \left(\sum_{i=1}^{10} \frac{V}{N}\right)^2 - \left(\sum_{i=1}^{10} \frac{V}{N}\right)^2$$

where V=voltage at each time point. Then mean square $$\frac{V^2}{N}$$

minus squared mean $$\left(\frac{V}{N}\right)^2.$$

If a true dysfunction exists, the measures revealing it must be reliably replicable. Replicability can be tested using the t-test at each time point:

$$t = \frac{(V_1 - V_2)}{|\sigma^2_{V1} + \sigma^2_{V2}|^{1/2}}$$

One could also use a cross-correlation across the entire wave with a threshold for minimum correlation which would be acceptable to replicate replicability. Once normative data are available for the mean and of the voltages at every time point, as a function of gestational age, this method can be used to test whether a fetal BAER is outside normal limits. If an abnormality is found with significance of P>0.05, for example, replication yields $p^2$<0.0025. Results from the two split halves may be combined (averaged) for display, with replicated significant results highlighted.

Brainstem Auditory Evoked Responses

Figure 2:
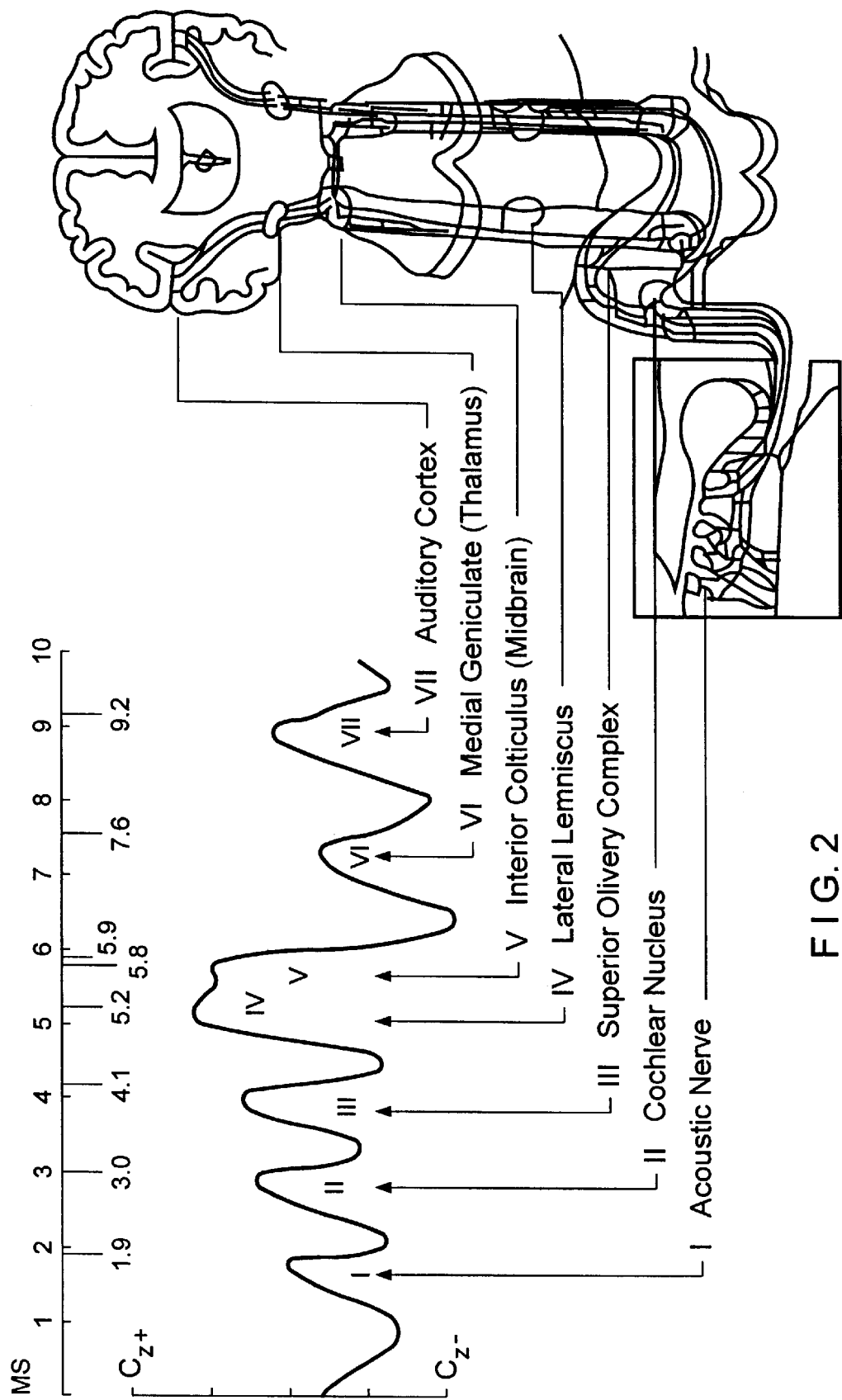
FIG. 2 is a chart showing normal Brainstem Auditory Evoked Response (BAER)
Figure 3:
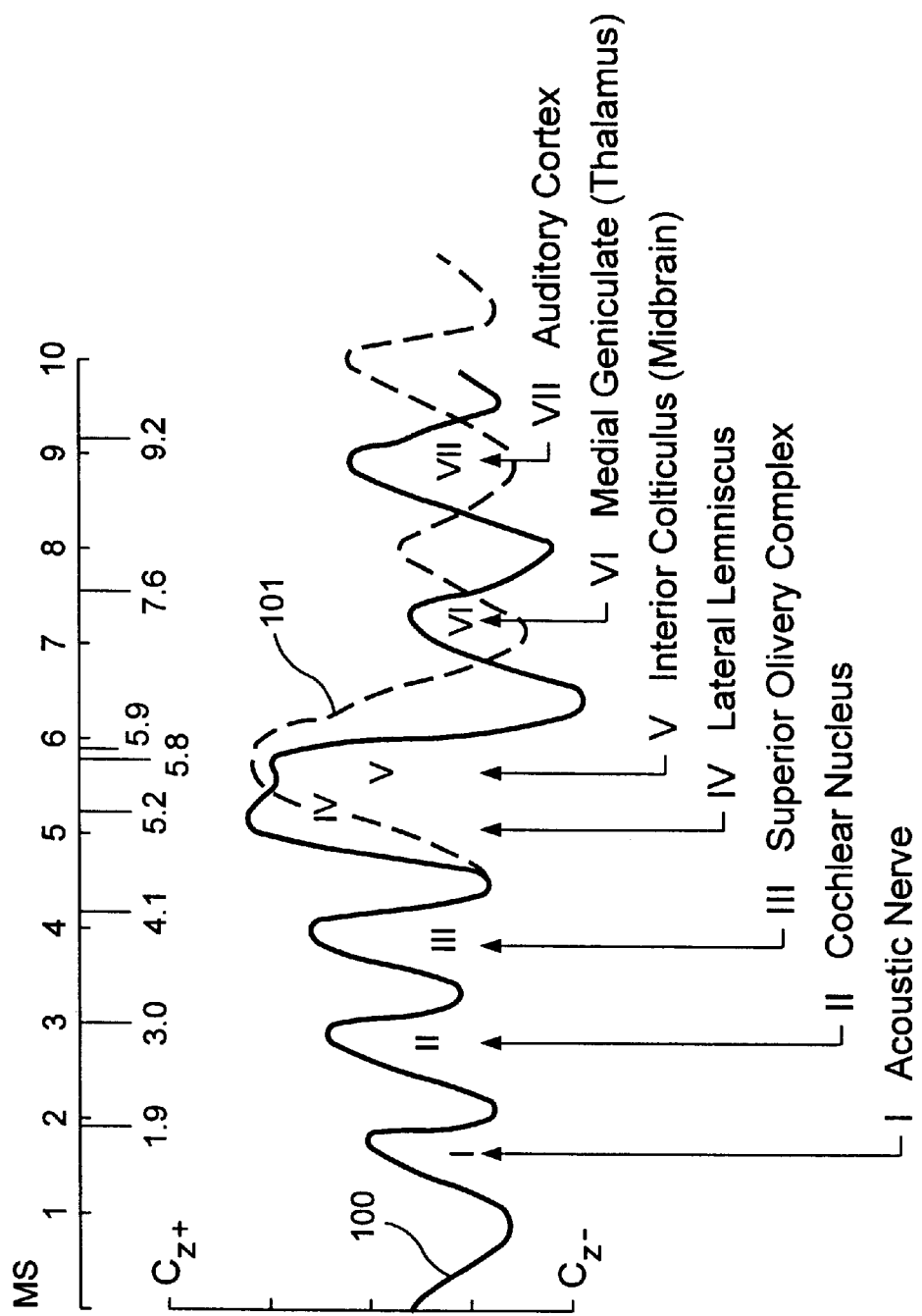
FIG. 3 is a chart comparing normal and abnormal BAERS.

The latencies of peaks of the BAER waveshape reflect transmission, along the auditory pathway, of neural electrical brain wave volleys, which are time-locked to presentation of an auditory stimulus. Each peak reflects the arrival of a volley of impulses at the successive levels of the auditory pathway, specifically the auditory nerve (7th cranial nerve), dorsal cochlear nucleus, superior olivary complex, lateral lemniscus, inferior colliculus, medial geniculate and auditory cortex (see FIG. 2). FIG. 3 shows a normal BAER 100 (solid line) and an abnormal BAER 101 (dash-dash line). The elapsed time (latency) from the delivery of each of the auditory stimuli, i.e., each click, to each of the peaks and the interpeak latencies, reflects the transmission time along the neural pathways. Such transmission times provide an estimate of the functional status of the neural structures and connecting pathways, and reflect complex factors which influence the level of polarization of the neuronal membrane and the availability of neuronal transmitters. Thus, the latencies of successive BAER provide figures of merit for the corresponding regions of the brainstem. Normative studies have shown the mean latencies of these peaks, and the inter-peak intervals, of the BAER to be precisely predictable and to stabilize at about 2 years of age to the characteristic adult values, with very small fluctuations (on the order of 200 microseconds for every peak) from age-appropriate normative values. Assessment of the peak latencies, therefore, has been found to have clinical implications in a wide variety of brain dysfunctions. However, such norms do not presently exist for the mean latencies of the peaks of the BAER of a fetus while it is still in the uterus (intrauterine).

The maturational changes in BAER morphology, especially the very rapid changes within the first months of life, provide an invaluable means for monitoring and following the development of the central nervous system (CNS). Studies have shown clear and consistent differences between pre-term and full-term neonates, often correlated to lesions or dysfunction of the peripheral and/or central auditory system or more extensive dysfunction resulting from global influences on the developing brain (Taylor, Pasman, Singh). Many of the deviations from BAER norms found in premature, and other high-risk infants, may have been present in the fetus. If they were to be detected by intrauterine assessment, it would provide an objective method for early CNS assessment and prognosis and, hopefully, eventual effective early intervention and remediation.

Optimal Digital Filtering

In one embodiment the Fetal Brainstem Monitor (FBM) utilizes a digital comb filter to improve the signal-to-noise ratio, a suitable digital comb filter being described in U.S. Pat. No. 4,705,049, incorporated by reference. In such a filter, the band pass frequencies are automatically selected, to form the teeth of the comb, using the phase variance parameter. That parameter is timed with the presence, and absence, of the audio stimulus. As mentioned previously, optimal digital filtering is an alternative to signal averaging to improve the signal-to-noise ratio. For example, in signal averaging the transducer usually produces 2048 auditory clicks at 5–20 per second. The BAER is in sync with the clicks, but the noise is random. When the responses are averaged, the noise is reduced proportional to the square root of the number of stimuli. This signal averaging procedure is relatively slow compared to the digital comb filter. Since ambient noise can be 10–20 microvolts, $1\sqrt{2048}$ would reduce noise to about 200–400 nanovolts. Since the BAER of the fetus will be about 100–200 nanovolts, the signal-to-noise ratio is unfavorable with conventional averaging.

In the digital comb filter, repeated samples of signal (presence of auditory stimulus) and noise (absence of auditory stimulus) are subjected to Fast Fourier Transform (FFT). At each frequency the variance of phase is computed for the sets of signal samples $\sigma_S^2$ and noise $\sigma_N^2$ samples. This allows computation at each frequency of an F-ratio, where $$F = \frac{\sigma_S^2}{\sigma_N^2}.$$

If F reaches statistical significance, i.e. (P>0.01), there is less variance at that frequency in the presence of stimulation than in ambient electrical noise, i.e., information is present concerning the stimulus. Those frequencies which are time-locked to the stimulus and which contribute to the evoked potential waveshape, show low-phase variance. Once the set frequency bands has been selected (the band pass teeth of the comb), then Inverse Fast Fourier Transform (IFFT) is applied to signals at those selected frequencies or intervals. In one embodiment of BAER, the band pass teeth of the digital filter comb, in the range 0–1400 Hz, were at 100–580 Hz, 600–640 Hz, 700–800 Hz, and 900–1400 Hz.

The following is a preferred example of optimal digital filtering as applied to BAER of the fetus as applied by the Fetal Brainstem Monitor (FBM).

Thirty-two "light averages" are computed, each derived from about 64 samples of the electrical activity recorded in the absence of stimulus ("Noise"). Using the Fast Fourier Transform (FFT), each segment is decomposed into series of sine and cosine terms which quantify the amplitude and phase of the components, at each frequency across the amplifier bandwidth of preferably 100 Hz to 1400 Hz (less preferably 50–2000 Hz) which when summed will reconstruct the electrical activity in that segment. The variance of phase at each frequency is calculated separately across the samples of 32 segments of signal and 32 samples of noise. The expression [variance of phase (signal)/variance of phase (noise)] is an F-ratio. Interpreted as a one-way ANOVA (Analysis of Variance), this gives the probability that information in the segment about the response to the stimulus (i.e., the BAER waveshape) is contained at that frequency. Using the F-ratio criterion, which may be based on experience, the coefficients in the FFT relating to all frequencies where information content is not significant are set to zero. Using the remaining terms which identify significant information content, the Inverse Fast Fourier Transform (IFFT) is performed, carrying the information from the frequency domain back into the time domain. The noise has thus been digitally identified and removed from the record. The resulting relatively noise-free signals are then averaged.

This optimal filter is applied to extract the BAER from brief samples of data. This permits real time monitoring, with rapid updates, which might be desirable during labor. This procedure may enable clean BAER waveshapes to be updated every 5 seconds with clearly defined peaks, and with repetition rates as high as 35/second.

The software (i) implements collection, with sufficient time resolution, of digitized samples of "signal" synchronized to stimulus delivery and samples of background "noise"; (ii) performs the FFT on each segment; (iii) computes the F-ratio of phase variance at each frequency; (iv) performs the indicated IFFT for optimal filtering; and (v) averages the noise-free signals to compute the BAER.

Data Evaluation

The data evaluation uses a quantitative assessment of the age-expected normality of the signal such as "Neurometrics" (the computerized quantitative analysis of brain electrical activity). In Neurometric analysis, features are extracted from the quantitative electroencephalogram (QEEG) and evoked potentials (EPs), transformed to obtain Gaussianity, compared to age-expected normative values, and expressed in standard deviation units of the normal population. The results can be displayed as color-coded topographic probability maps of brain function, or color-coded segments of a curve in the time domain (voltage vs. latency). The normative data are free of ethnic bias. Utilizing these methods greatly enhances the sensitivity, specificity and clinical utility of such data. Profiles of QEEG and EP abnormalities can be mathematically described and are distinctive of different neuropsychiatric and neurological populations. A significant relationship between QEEG subtype membership established by cluster analysis, treatment outcome and evolution of disorders has also been established, see U.S. Pat. No. 5,083,571.

In order to provide automatic evaluation of the filtered BAER, an algorithm will be developed, which is applicable to fetal BAER, to identify the latency of each peak by automatic peak-detection. After 3-point smoothing of the filtered average, the resulting BAER is amenable to automatic peak detection by a simple procedure which hunts for zero-values of the second derivative and prints the resulting series of time points. The computed peaks are marked on the optimally filtered BAER and superimposed on a normal template. As shown in FIG. 3, a normal template is curve 100. The peaks (marked *) of an abnormal BAER 101 are marked on the same FIG. 3.

In order to assess the BAER thus recorded from an individual fetus, these latencies are compared to normative data. Such normative data will be collected from a group of pre-term and full-term infants shortly after birth and from pre-natal intra-uterine records collected from an adequate sample of mothers every week during the last trimester of pregnancies which resulted in birth of a normal infant. The Neurometric norming approach, which has been demonstrated to greatly enhance the clinical utility of the EEG in psychiatric and neurological disorders, will be applied to this data.

The Subject Population for the collection of normative data will be volunteers in the last trimester of pregnancy. These women will be between the ages of 25–35 years and with uneventful pregnancies. Informed consent will be obtained in each volunteer.

In much the same way, at certain junctures it may be desirable to use the individual fetus as its "norm", thus emphasizing change from an identified start point.

For testing, subjects will be comfortably seated or reclining. The auditory stimulator will be placed on their abdomen and the recording electrode will be placed at a point determined to be near the fetal head, determined by the obstetrician. The reference electrode will be pasted on the thigh.

The levels of auditory stimulation will be within that used in other routine prenatal examinations, i.e., sonograms. Accurate waveshapes can be obtained at any desired interval, providing a developmental brainstem evaluation during pregnancy or a monitor of brainstem state during labor and delivery.

What is claimed is:

1. A method of monitoring a brain wave response of a fetus in utero, comprising the steps of:

(a) removably connecting an auditory transducer to an abdomen of a mother of the fetus;

(b) removably connecting at least one biosensor electrode to the mother's abdomen to detect brain wave activity in the fetus;

(c) pulsing the transducer to emit pulsed audible sounds at predetermined times;

(d) detecting, for each pulsed audible sound, a series of voltage oscillations corresponding to brain stem auditory evoked responses (BAER) of the fetus which are time-locked to the corresponding audible sound; and (e) converting the BAER analog output to BAER digital data.

2. The method of monitoring as in claim 1, further comprising the step of improving a signal to noise ratio of the BAER digital data using a computer-based QEEG (Quantitative EEG) system.

3. The method of monitoring as in claim 2, further comprising the step of displaying results of the QEEG analysis as an indication of the status of brain function of the fetus.

4. The method of monitoring as in claim 1, wherein, in step (b), the at least one biosensor electrode comprises an array of biosensor electrodes connected to the mother's abdomen.

5. The method of monitoring as in claim 1, wherein, in step (c), the pulsing of the transducer generates the audible sounds from the transducer at a predetermined rate selected to optimize recording of data.

6. The method of monitoring as in claim 2, further comprising the step of passing the BAER digital data through a a digital comb filter having a plurality of band pass frequency ranges within an overall frequency range of 50–2000 Hz.

7. The method of monitoring as in claim 6, further comprising the steps of:
  passing the data from the digital comb filter through a Fast Fourier Transform (FFT) arrangement to transform the data to a frequency domain;
  elminating non-significant portions of the data from the digital comb filter using the FFT arrangement; and
  transforming significant coefficients of the data from the FFT arrangement back into a time domain using an Inverse Fast Fourier Transform (IFFT) arrangement.

8. The method of monitoring as in claim 2, further comprising the step of comparing the BAER digital data to reference BAER data from a control group to determine one of an abnormality and normality of the BAER of the fetus being monitored.

9. The method of monitoring as in claim 2, further comprising the step of comparing successive recordings of the BAER digital data from the fetus being monitored using an initial recording from the fetus being monitored as a "self-norm" to determine a degree of change from an initial state.

10. A Fetal Brain Monitor for monitoring a brain wave response of a fetus in utero, comprising:
  (a) an auditory transducer producing pulsed audible sounds and adapted to be placed on an abdomen of a mother of the fetus;
  (b) at least one biosensor electrode adapted to be placed on the mother's abdomen for detecting electrical activity of a brain of the fetus;
  (c) a pulsing arrangement pulsing the transducer so that it emits pulsed audible sounds at predetermined times;
  (d) an amplifier connected to the at least one biosensor electrode to amplify brain stem auditory responses (BAER) of the fetus detected by the at least one biosensor electrode which are time-locked to the sounds;
  (e) an analog/digital converter converting the analog BAER data to BAER digital data;
  (f) a computer-based QEEG (Quantitative EEG) system improving a signal to noise ratio of the BAER digital data and analyzing the BAER digital data; and
  (g) a display displaying results of the QEEG analysis as an indication of a status of the BAER.

11. The Fetal Brain Monitor as in claim 10, wherein the at least one biosensor electrode includes 3 electrodes.

12. The Fetal Brain Monitor as in claim 10, wherein the pulsing arrangement generates audible sounds from the transducer at a predetermined optimal rate per second.

13. The Fetal Brain Monitor as in claim 10, wherein the computer system includes a digital comb filter having a plurality of band pass frequency ranges in an overall frequency range of 50–2000 Hz.

14. The Fetal Brain Monitor as in claim 13, further comprising:
  a Fast Fourier Transform (FFT) arrangement transforming the digital data which passes through the digital comb filter into a frequency domain and eliminating non-significant coefficients from the data; and
  an Inverse Fast Fourier Transform (IFFT) arrangement transforming significant coefficients from the data transformed by the FFT arrangement back into a time domain.

15. The Fetal Brain Monitor as in claim 10, further comprising:
  an arrangement comparing the BAER digital data to comparative BAER data from a normal group of fetuses to determine one of an abnormality and normality of the BAER.

16. The Fetal Brain Monitor as in claim 10, further comprising:
  an arrangement comparing to one another successive recordings of BAER digital data from the fetus being monitored using an initial recording as a "self-norm" to determine a degree of change from an initial state.

17. The method of monitoring as in claim 6, further comprising the step of setting the band pass frequencies of the digital comb filter by comparing a SIGNAL sample of data corresponding to a time period during which pulsed audible sounds were generated by the transducer and a NOISE sample of data corresponding to a time period during which no pulsed audible sounds were generated by the transducer.

18. The method of monitoring as in claim 7, wherein after the significant coefficients of the data from the FFT arrangement have been transformed back into a time domain using the IFFT arrangement, mean amplitudes and variances of amplitudes are computed at each of a plurality of sampling points corresponding to times during which brain responses to the pulsed audible signals are generated to produce a wave corresponding to the BAER.

19. The method of monitoring as in claim 18, further comprising the step of smoothing successive peaks of the wave.

20. The method according to claim 18, wherein significant coefficients of the data from the FFT arrangement are identified by analyzing phase variations of the data from time periods during which pulsed audible signals are generated as compared to time periods during which pulsed audible signals are not generated.

* * * * *